(12) United States Patent
Nonaka

(10) Patent No.: US 6,444,648 B1
(45) Date of Patent: Sep. 3, 2002

(54) LEISHMANIASIS REMEDY CONTAINING GLUCOPYRANOSE DERIVATIVE AS THE ACTIVE INGREDIENT

(75) Inventor: Shigeo Nonaka, Naha (JP)

(73) Assignee: University of the Ryukyu, Okinawa (JP)

( * ) Notice: Subject to any disclaimer, the term of this patent is extended or adjusted under 35 U.S.C. 154(b) by 0 days.

(21) Appl. No.: 09/529,333

(22) PCT Filed: Oct. 8, 1998

(86) PCT No.: PCT/JP98/04537
§ 371 (c)(1),
(2), (4) Date: Jul. 17, 2000

(87) PCT Pub. No.: WO99/18975
PCT Pub. Date: Apr. 22, 1999

(30) Foreign Application Priority Data

Oct. 9, 1997 (JP) ............................................. 9-277656

(51) Int. Cl.[7] ........................ A01N 43/04; A01N 61/00; A01N 43/00
(52) U.S. Cl. .............................. 514/42; 514/1; 514/23; 514/25; 514/183
(58) Field of Search ........................... 514/183, 23, 25, 514/1, 42

(56) References Cited

U.S. PATENT DOCUMENTS 5,496,830 A  3/1996  Shapiro et al. ............. 514/283

FOREIGN PATENT DOCUMENTS

| EP | 0 226 381 A2 | 6/1987 |
|----|--------------|--------|
| EP | 0 553 786 A2 | 8/1993 |
| JP | 4-74359 | 11/1992 |
| JP | 6-41175 | 2/1994 |
| WO | WO 90/03174 | 4/1990 |

OTHER PUBLICATIONS

Matsumoto, et al.; "Restoration of Immune responses in tumopr-bearing mice by ONO-4007, an antitumor lipid A derivative{"; Immunopharmacology, vol. 36, No. 1, (Apr. 1997) pp. 69–78.

Hattori Y., et al.; "Lipid A and the lipid A analogue anti-tum or compound ONO-4007 induce nitric oxide synthase in vitro and in vivo"; European Journal of Pharmacology Molecular Pharmacology Section, vol. 291 (1995) pp. 83–90.

Kobayashi M., et al.; "ONO-4007, a new synthetic lipid A derivative, induces differentiation of rat myelomonocytic leukemia cells in vitro and in vivo"; Experimental Hematology, vol. 22 (1994) pp. 454–459.

Tandon, J.S., et al.; "Iridoids; A New class of Leishmanicidal A Gents from Nyctanthes Arobrtristis"; Journal of Natural Products, vol. 54; N9o. 4.; (Jul. –Aug. 1991) pp. 1102–1104.

*Primary Examiner*—Jezia Riley
(74) *Attorney, Agent, or Firm*—Knobbe, Martens, Olson, Bear, LLP

(57) ABSTRACT

A leishmaniasis preventing and/or treating agent having 2-deoxy-2-[(3S)-(9-phenylnonanoyloxy)tetradecanoyl]amino-3-O-(9-phenylnonanoyl)-4-O-sulfo-α-D-glucopyranose represented by a formula (I) or a non-toxic salt thereof as an effective ingredient.

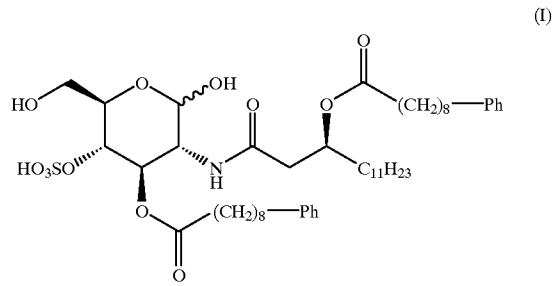

2-deoxy-2-[(3S)-(9-phenylnonanoyloxy)tetradecanoyl]amino-3-O-(9-phenylnomanoyl)-4-O-sulfo-α-D-glucopyranose represented by a formula (I) or a non-toxic salts effectively functions to prevent and/or treat leishmaniasis, and is a highly safe compound.

5 Claims, No Drawings

LEISHMANIASIS REMEDY CONTAINING GLUCOPYRANOSE DERIVATIVE AS THE ACTIVE INGREDIENT

This application is the U.S. National Phase under 35 U.S.C. §371 of International Application PCT/JP98/0437, filed Oct. 8, 1998, which claims priority based on JP 9-277656, filed Oct. 9, 1997.

BACKGROUND OF THE INVENTION

1. Technical Field to Which the Invention Belongs

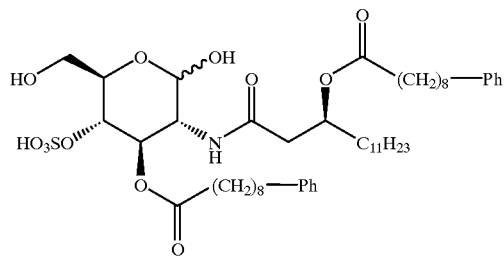

The present invention relates to a leishmaniasis preventing and/or treating agent having 2-deoxy-2-[(3S)-(9-phenylnonanoyloxy)tetradecanoyl]amino-3-O -(9-phenylnonanoyl)-4-O-sulfo-α-D-glucopyranose represented by a formula (I) or a non-toxic salt thereof as an effective ingredient.

2. Prior Art

The leishmaniasis is a parasite disease common to human beings and animals, which is induced by leishmaniasis parasites via Phlebotomus flies as blood-sucking insects. At present, the disease is widely spread, mainly in developing countries, in old world such as India, China and Mediterranean Sea and new world such as the Middle and South American areas, and is a infectious disease that is estimated to have about 12,000,000 to 14,000,000 patients all over the world. This disease is designated as one of the six greatest diseases with which WHO should grapple. The leishmaniasis is clinically classified into three types: visceral type, cutaneous type and mucocutanaous type. Among them, the visceral leishmaniasis is a serious disease that results in death if it is left without treatment.

When a person is infected with a leishmaniasis infectious species, the leishmaniasis appears after a latent period from one or two weeks to several months. The symptom, which depends on the respective types, includes fever, lassitude, weight loss, anemia, hepatosplenomegray, swelling of lymph node, etc. for the visceral leishmaniasis. The number of leukocytes decreases, which makes the patient weak against other infectious diseases and becomes systemic weak. The cutaneous leishmaniasis spreads from boundaries between mucous membrane and skins, and gradually destroys surrounding cartilages. The face and the looks are conspicuously destroyed, and occasionally the nasal septum is infected, finally a nose is sometimes taken off. The cutaneous leishmaniasis causes a nodule on an exposed portion of the human body and may causes occasionally an ulcer. Although spots and swellings never seen occur on the skin, they are accompanied by no pain.

As therapeutic agents for such leishmaniases, various medicines such as Amphotericin B, Bleomycin, Interleukin 2, Interferon γ and Pentamidine have been used. (See Koff A. B. etal., J. Ame. Acad. Dermatol, 31, 639 (1994)). Among them, it is known that an antimony-based medicine is a specific. Further, it is reported that a lipopolysaccaride (LPS) is effective for cellular death resulting from the leishmaniasis infectious species (See Jacques, M. Eur. J. Immunol., 17, 203 (1987)).

DISCLOSURE OF THE INVENTION

However, since these medicines all have strong side effects, doctors need to pay their meticulous attentions to their use. Therefore, development of more effective and safer medicine by selectively acting upon leishmaniasis is desired.

In JP-B 4-74359 In JP-B 4-74359, it is disclosed that a compound used in the present invention, 2-deoxy-2-[(3S)-(9-phenylnonanoyloxy)tetradecanoyl]-amino-3-O-(9-phenylnonanoyl)-4-O-sulfo-α-D-glucopyranose, which is represented by the formula (I) and a non-toxic salt thereof (hereinafter abbreviated as "the compound in the present invention") have lipid A-like activity and exhibit immuno-enhancing activity (macrophages activating effect, B cell mitogenic activity, non-specific antibody producing activity, cellular immunity enhancing activity, etc.) and antitumor activity (interferon inducing activity, interferon producing activity, TNF inducing activity, etc.). Various kinds of non-non-toxic salts of the compound of the present invention are disclosed in JP-A 6-41175.

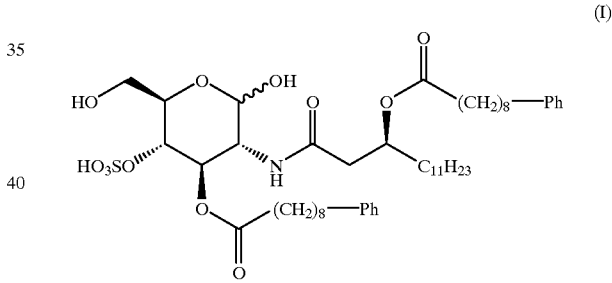

However, the activity of the compound in the present invention upon the leishmaniasis has not been reported at all.

Having streneously made investigations to discover a compound that acts upon prevention and/or therapy of the leishmaniasis and is highly safe, the present inventors discovered that 2-deoxy-2-[(3S)-(9-phenylnonanoyloxy)-tetradecanoyl]amino-3-O-(9-phenylnonanoyl)-4-O-sulfo-α-D-glucopyranose having the formula (I) and a non-toxic salt thereof accomplish the object.

GIST OF THE INVENTION

A leishmaniasis preventing and/or treating agent having 2-deoxy-2-[(3S)-(9-phenylnonanoyloxy)tetradecanoyl] amino-3-O-(9-phenylnonanoyl)-4-O-sulfo-α-D-glucopyranose represented by a formula (I) or a non-toxic salt thereof as an effective ingredient.

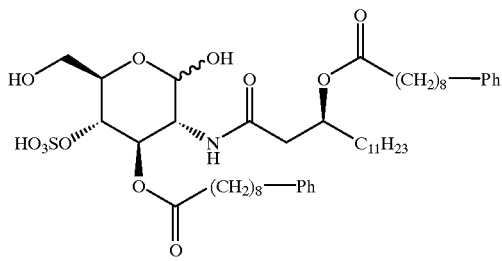

The 2-deoxy-2-[(3S)-(9-phenylnonanoyloxy) tetradecanoyl]amino-3-O-(9-phenylnonanoyl)-4-O-sulfo-α-D-glucopyranose represented by a formula (I) or the non-toxic salts are effective to prevent and/or treat leishmaniasis, and is a highly safe compound.

DETAILED DESCRIPTION OF THE INVENTION

The present invention relates to a leishmaniasis preventing and/or treating agent having 2-deoxy-2-[(3S)-(9-phenylnonanoyloxy)tetradecanoyl]-amino-3-O-(9-phenylnonanoyl)-4-O-sulfo-α-D-glucopyranose represented by the formula (I) or a non-toxic salt thereof as an effective ingredient.

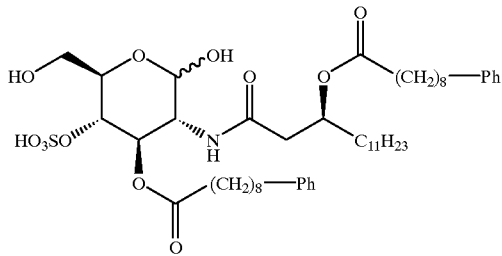

1. Salts

The compound in the present invention represented by the formula (1) is converted to corresponding salts according to known methods. The salts which are non-toxic and water-soluble are preferred. Appropriate salts include salts of alkali metals (potassium, sodium, etc.), salts of alkaline-earth metals (calcium, magnesium, etc.), ammonium salts and salts of pharmaceutically-acceptable organic amines (tetramethyl ammonium, triethylamine, methylamine, dimethylamine, cyclopentylamine, benzylamine, phenethylamine, piperidine, monoethanolamine, diethanolamine, lysine, arginine, N-methyl-D-glucamine, tris(hydroxymethyl)methylamine, etc.).

The compounds in the present invention represented by the formula (I) or its salts may be converted to their hydrates according to known methods.

2. Methods for producing the compound in the present invention

As regards various kinds of non-toxic salts of the compound in the present invention represented by the formula 1, in JP-A 6-41175, methods for producing sodium salts thereof are described in detail in the Examples 2, 3, 5 and 6 and methods for producing tris(hydroxymethyl) methylammonium salt thereof in the Example 4.

3. Toxicity

The toxicity of the compound in the present invention is very low, and can be judged to be enough safe as to be used as a medicine. For example, a sodium salt of 2-deoxy-2-[(3S)-(9-phenylnonanoyloxy)tetradecanoyl]amino-3-O-(9-phenylnonanoyl)-4-O-sulfo-α-D-glucopyranose exhibits an $LD_{50}$ value of 60 to 70 mg/kg in a case of intraveneous administration to SD-series male and female rats.

4. Application to medicine

The compounds in the present invention is effective for preventing and/or treating the leishmaniasis in animals including human beings, especially in the human beings.

In order to use the compound in the present invention represented by the formula (1), its non-toxic salt or their hydrate for the above purpose, it is usually administered systemically or topically and orally or parenterally.

Each of them is administered at a dosage, which depends upon ages, weights, symptoms, therapeutic effects, administrating ways, treatment periods, etc., ordinarily orally in a range of 1 mg to 1000 mg/one administration for an adult once to several times a day, or parenterally (preferably intravenously) in a range of 1 mg to 100 mg/one administration for an adult once to several times a day or continuously intravenously in a range of 1 to 24 hours a day.

As mentioned above, since the dosage depends upon various conditions, an amount smaller than the above dosage may be sufficient, or an amount beyond the above range may be necessary.

When the compound in the present invention is administrated, it is used in the form of solid compositions, liquid compositions and other compositions for the oral administrations, and in the form of injection solutions, medicines for external applications, suppositories, etc. for the parenteral administrations.

The solid compositions for the oral administrations include tablets, pills, capsules, powders, granulated medicines, etc.

The capsules include hard capsules and soft capsules.

In such solid compositions, one or more active materials are mixed with at least one inert diluent, for example, lactose, mannitol, glucose, hydroxypropyl cellulose, finely crystalline cellulose, starch, polyvinylpyrrolidone, or magnesium metasilicate aluminate. According to a usual way, the composition may include, besides such inert diluents, additive(s), for example, a lubricant such as magnesium stearate, a disintegrant such as fibrous calcium glycolate, a stabilizer such as lactose, and a dissolution aid such as glutaminic acid or aspartic acid. The tablets or pills may be coated with a film of a gastric or enteric material such as white sucrose, gelatin, hydroxypropylcellulose, hydroxypropylmethylcellulose phthalate, or may be coated with two or more layers. A capsule of an absorbable material such as gelatin is encompassed.

The liquid compositions for the oral administration includes pharmaceutically acceptable emulsions, solutions, syrups, elixirs, etc. In such a liquid composition, one or more active materials are contained in an ordinarily used inert diluent (for example, purified water, ethanol). This composition may contain, besides the inert diluents, auxiliary agents (e.g. a wetting agent, a suspending agent), sweetenings, flavors, aromatics and preservatives Other compositions for the oral administration includes a spraying medium which contains one or more active agents and is formulated according to a known method. This composition may contain, besides the inert diluents, a stabilizer such as sodium hydrogen sulfite, an isotonicity buffer agent such as sodium chloride, and an isotonic agent such as sodium chloride or citric acid. A method for producing spraying medium is described in detail in U.S. Pat. Nos. 2,868,691 and 3,095,355, for example.

The injection solution medium in the present invention for the parenteral administration includes aseptic aqueous and/or non-aqueous solvent, suspension, emulsion. The aqueous solution and suspension include distilled water for injection and physiological saline, for example. The non-aqueous solvent and suspending medium include propylene glycol, polyethylene glycol, plant oil such as olive oil, alcohols such as ethanol, Polysorbate 80 (registered trademark), etc. Further, aseptic aqueous and non-aqueous solvents, suspensions and emulsions may be used in a mixed state. Such compositions may include auxiliary agents such as antisepatic, wetting agent, emulsifier, dispersant, stabilizer (for example, lactose), dissolution aid (for example, glutaminic acid, aspartic acid). They are sterilized by filtering them through bacteria-retaining filters, mixing a germicide thereinto or irradiating light thereon. They may be produced in the form of an aseptic solid compositions, and used after being sterilized or dissolved in aseptic distilled water for injection or other solvents, for example, before using a freeze-dried product thereof.

Other compositions for the parenteral administrations include external-use solutions, ointments, liniments, suppositories for intrarectal administrations, pessary for intravaginal administrations, etc.

EXAMPLES

In the following, the present invention will be described in detail based on examples, but the present invention is not limited to them.

Example 1

Effects Upon Leishmaniasis-infected Mice (Experimental method)

L. amazonesis was inoculated to tail root portions of BALB/c mice to prepare L. amazonesis-infected mice, and the mice were used 6 week after the infection. These mice were divided into four groups as mentioned below, infected foci (tail root portions) were photographed with lapse of time, and the effects upon them were examined in terms of [by means of] shrinkage degrees of the skin foci. The shrinkage degree of the skin focus was found by measuring a major axis of ulcer or node. The magnitude before administration was taken as 100 and the magnitude 8 weeks after administration was calculated according to the following calculation formula. The results are shown in Table 1.

Group A (Control group)
  Only a solvent (55% ethanol-4.5% glucose liquid) was injected topically into a focus twice a week for 8 weeks.
Group B (Control group)
  Only a solvent (55% ethanol-4.5% glucose liquid) was injected intraperitoneally twice a week for 8 weeks.
Group C (Topically injected group)
  A solution in which the sodium salt of the compound in the present invention represented by the formula (1) was dissolved in the solvent was injected topically into a focus twice a week for 8weeks at a rate of 30 mg/kg.
Group D (intraperitoneally injected group)
  A solution in which the sodium salt of the compound in the present invention represented by the formula (1) was dissolved in the solvent was injected intraperitoneally twice a week for 8 weeks at a rate of 30 mg/kg.

$$\text{Shrinkage degree of the skin focus} = \frac{\text{Major axis of the focus 8 weeks after administrtion}}{\text{Major axis of the focus before administration}} \times 100$$

TABLE 1

| Group | Average focus shrinkage degree |
|-------|-------------------------------|
| A     | 220.5 (n = 7)                 |
| B     | 289.3 (n = 8)                 |
| C     | 138.9 (n = 7)                 |
| D     | 178.5 (n = 6)                 |

From Table 1, it is seen that the compound in the present invention effectively shrunk the focal infection of the leishmaniasis-infected mice. Further, the skin focus was completely cured with respect to three mice in Group C.

Formulating Example I

The following ingredients were mixed according to an ordinary method, and the resulting solution was sterilized according to an ordinary method. Then, the solution was filled each in an amount of 1 ml into ampules, which were freeze dried according to an ordinary method, thereby obtaining 100 ampules each containing 50 mg of an active ingredient.

| | |
|---|---|
| Sodium salt of 2-deoxy-2-[(3S)-(9-phenylnonanoyloxy)-tetradecanoyl]amino-3-O-(9-phenylnonanoyl)-4-O-sulfo-α-D-glucopyranose | 5.00 g |
| 55% ethanol | 100 ml |

What is claimed is:

1. A method for preventing and/or treating a disease caused by a leishmaniasis infectious species, comprising administrating 2-deoxy-2-[(3S)-(9-phenylnonanoyloxy)tetradecanoyl]amino-3-O-(9-phenylnomanoyl)-4-O-sulfo-α-D-glucopyranose, represented by Formula (I)

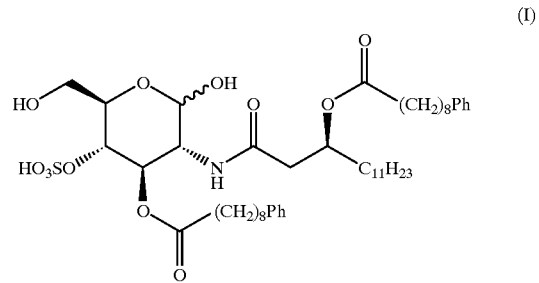

or a non-toxic salt thereof to a mammal which is infected with or susceptible to species of the genus Leishmania, in an amount effective to prevent and/or treat a disease associated with the infection.

2. The method according to claim 1, wherein the disease is leishmaniasis.

3. The method according to claim 1, wherein the mammal is a human.

4. The method according to claim 1, wherein the administration is orally conducted.

5. The method according to claim 1, wherein the administration is parenterally conducted.

* * * * *